United States Patent [19]
Shuter

[11] Patent Number: 5,490,858
[45] Date of Patent: Feb. 13, 1996

[54] METHOD AND APPARATUS FOR HANDLING SUTURING NEEDLES

[76] Inventor: David Shuter, 8642 Marlamoor La., Palm Beach Gardens, Fla. 33412

[21] Appl. No.: 275,827

[22] Filed: Jul. 15, 1994

Related U.S. Application Data

[63] Continuation of Ser. No. 62,965, May 14, 1993, abandoned.

[51] Int. Cl.⁶ ................................................. A61B 17/00
[52] U.S. Cl. ........................ 606/148; 606/139; 606/144; 606/233
[58] Field of Search ................................. 606/148, 139, 606/222, 158, 232, 144, 147, 149, 150, 233; 604/192, 263; 223/109 R

[56] References Cited

U.S. PATENT DOCUMENTS

| | | | |
|---|---|---|---|
| 1,139,942 | 5/1915 | Wightman et al. | 223/109 R |
| 2,058,340 | 10/1936 | Miller | 223/109 R |
| 2,818,206 | 12/1957 | Anderson | 223/109 R |
| 3,225,981 | 12/1965 | Micale | 223/109 R |
| 3,878,848 | 4/1975 | Hiebert . | |
| 4,380,292 | 4/1983 | Cramer | 604/192 X |
| 4,392,495 | 7/1983 | Bayers . | |
| 4,416,267 | 11/1983 | Garren et al. . | |
| 4,755,170 | 7/1988 | Golden | 604/192 X |
| 4,819,640 | 4/1989 | Narayanan et al. | 606/148 |
| 4,969,893 | 11/1990 | Swor . | |
| 4,971,075 | 11/1990 | Lee . | |
| 4,981,149 | 1/1991 | Yoon et al. . | |
| 4,991,594 | 2/1991 | Angelchik . | |
| 5,064,411 | 11/1991 | Gordon, III . | |
| 5,127,412 | 7/1992 | Cosmetto et al. . | |
| 5,178,157 | 1/1993 | Fanlo | 604/174 |
| 5,179,964 | 1/1993 | Cook . | |
| 5,342,375 | 8/1994 | Lemole | 606/148 |

FOREIGN PATENT DOCUMENTS

| | | | |
|---|---|---|---|
| 2620339 | 3/1989 | France | 604/263 |
| 2198644 | 6/1988 | United Kingdom | 604/192 |
| 18184 | 10/1992 | WIPO | 604/265 |

OTHER PUBLICATIONS

Vicki Fox: AORN Journal; "Clinical Issues"; pp. 264–266; Jan. 1992 vol. 55, No. 1.
Plastic and Reconstructive Surgery; pp. 144–145; vol. 90, No. 1 Jul. 1992.
Plastic and Reconstructive Surgery; pp. 960–961; vol. 91, No. 5 Apr. 1993.

*Primary Examiner*—Stephen C. Pellegrino
*Assistant Examiner*—Michael Peffley
*Attorney, Agent, or Firm*—Quarles & Brady

[57] ABSTRACT

A method and apparatus for handling suture needles, and for suturing, is disclosed in which a sterile, needle pervious retaining material is provided. A suturing needle contaminated with biological material is thrust into the retaining material to permit the tying of a knot with a reduced risk of needle sticks. Structure for grasping the retaining material and for shielding portions of the apparatus from penetration by the needle can also be provided.

3 Claims, 8 Drawing Sheets

METHOD AND APPARATUS FOR HANDLING SUTURING NEEDLES

This is a continuation of application Ser. No. 08/062,965, filed May 14, 1993, now abandoned.

BACKGROUND OF THE INVENTION

1. Field of the Invention

This invention relates generally to surgical methods and apparatus, and more particularly to methods and apparatus for the handling of suturing needles.

2. Description of the Relevant Art

Needle sticks are an ever-present concern when suturing and otherwise handling contaminated suturing needles. Such needle sticks can transmit infectious diseases such as hepatitis or Acquired Immune Deficiency Syndrome (AIDS). There are many opportunities for needle sticks to occur during the suturing process. The suturing needle is first positioned in a needle holding instrument. The needle is then manipulated to place the suture where desired. The needle is removed from the needle holder, and a suture knot is tied by the surgeon. The suture needle typically dangles freely at the end of the suture while the suture knot is tied. The suture needle is then again secured to the needle holder, whereupon another suture is placed. After the suturing process is completed, the suture needle is handed to a nurse or other assistant. Needle sticks regularly occur while surgeons are placing sutures, and sometimes occur when the suturing needle is handed from the surgeon to an assistant, or thereafter between assistants.

There is an acute need for a method and/or apparatus which will reduce the number of needle sticks, but will interfere only minimally with the suturing process. One such method is described in *Plastic and Reconstructive Surgery*, Volume 90, Number 1, Jul. 1992. A method is shown wherein the suture needle is positioned with the concave curve of the needle facing the jaws of the needle holder. The sharp tip of the needle lies against the box of the needle holder where the two jaws are joined. The point is thereby shielded from the physician, the assistants, and the patient. Another method is disclosed in *Plastic and Reconstructive Surgery*, Volume 91, Number 5, Apr. 1993. By this method, the needle holder is used to clamp the suture just proximal to its juncture with the needle. The needle dangles freely and does not form a solid resistance, and is pushed away upon accidental contact. Each of these methods, however, requires that the suture needle be secured to the needle holder. These techniques do not prevent needle sticks during tying, however, and still present dangerous needle stick opportunities during the passing process, both to the surgeon and to the assistant.

SUMMARY OF THE INVENTION

It is an object of the invention to reduce the likelihood of needle sticks during suturing, and while handling suture needles.

It is another object of the invention to provide a method and apparatus for preventing needle sticks when handling a suture needle which will not significantly interfere with the suturing process.

It is another object of the invention to reduce, at a minimum cost, the likelihood of needle sticks during suturing processes.

These and other objects are accomplished by a method and apparatus for handling suture needles in which a sterile, needle pervious material is provided in a dimension capable of being grasped with one hand. The suture needle is thrust into the retaining material and is held by the retainer while the suture is tied. The needle is then removed from the retainer to place another suture.

Apparatus according to the invention preferably is dimensioned for retention by one hand. The needle pervious material can be constructed from any non-toxic material which can retain the needle when the needle is thrust into the material. Silicone is a currently preferred material. The retainer can be provided in a number of different shapes and sizes, and can be manufactured in various configurations and constructions within the spirit of the invention. Structure can be provided to further protect the physician during insertion and removal of the needle into the retaining material of the retainer. Such structure preferably comprises needle impervious caps, protrusions or linings which will at least partially shield the hand of the physician from the needle. Structure can also be provided to assist the physician in grasping the retainer. The apparatus can be provided with an outer package which maintains the sterility of the product prior to use.

According to the method of the invention, a suture needle is placed in a needle holder and the suture is placed. With the needle still in the needle holder, the needle is thrust into the retaining material of the retainer and released from the needle holder. The surgeon can then tie a suture knot, either while holding the retainer in one hand or while allowing the retainer to dangle freely at the end of the suture. The needle is again clamped to the needle holder, and is removed from the retaining material. The surgeon can put the retainer down, or hold it in a free hand. The needle holder is then manipulated to place another suture. The process is repeated as many times as are necessary. When the suturing process is completed, the needle can be thrust back into the retaining material for purposes of handing the needle to an assistant, and for subsequent handling and disposal.

BRIEF DESCRIPTION OF THE DRAWINGS

There are shown in the drawings embodiments which are presently preferred, it being understood, however, that the invention is not limited to the precise arrangements and instrumentalities shown, wherein.

DETAILED DESCRIPTION

Figure 1:
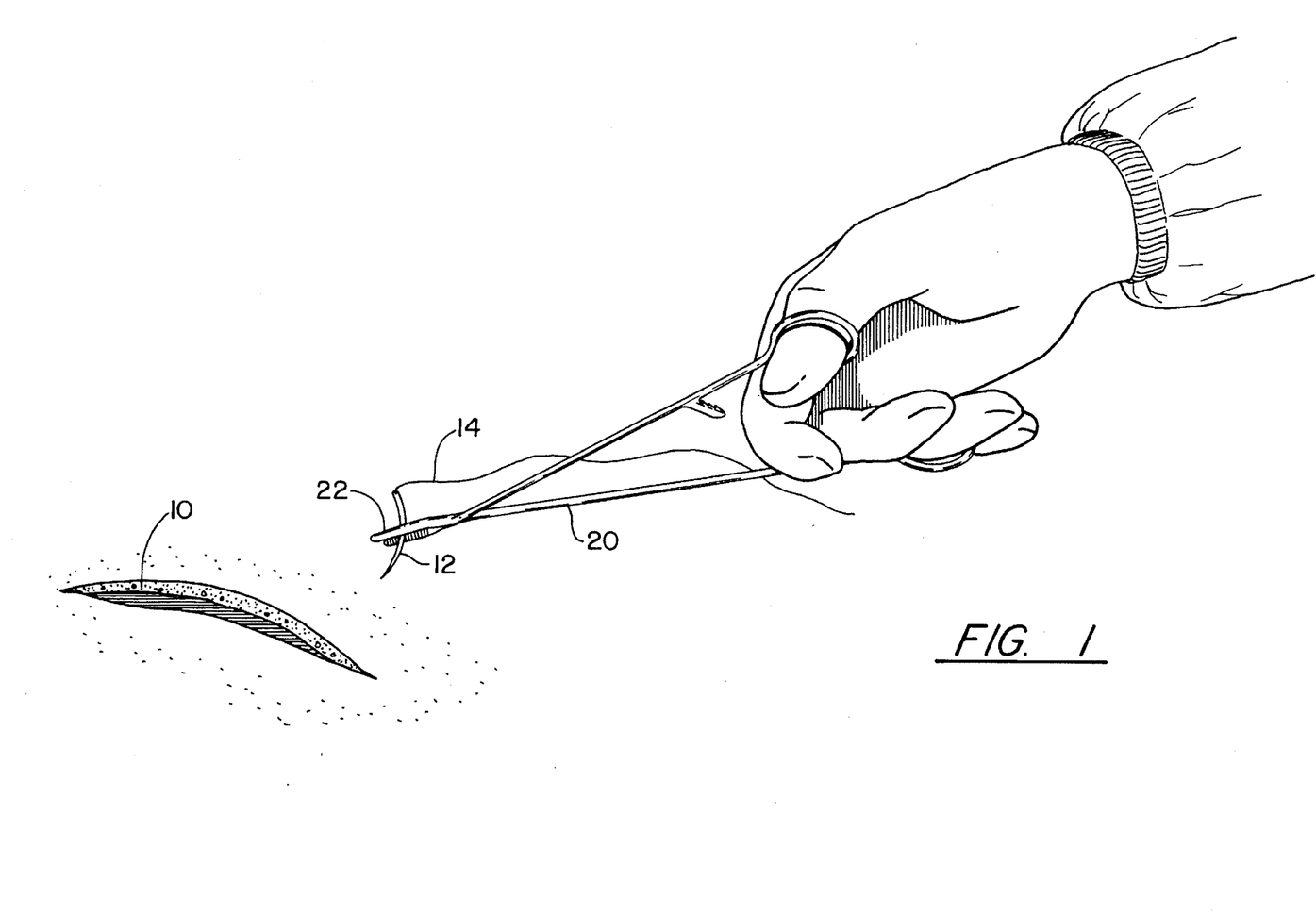
FIG. 1 is a perspective view illustrating the placement of a suture.
Figure 2:
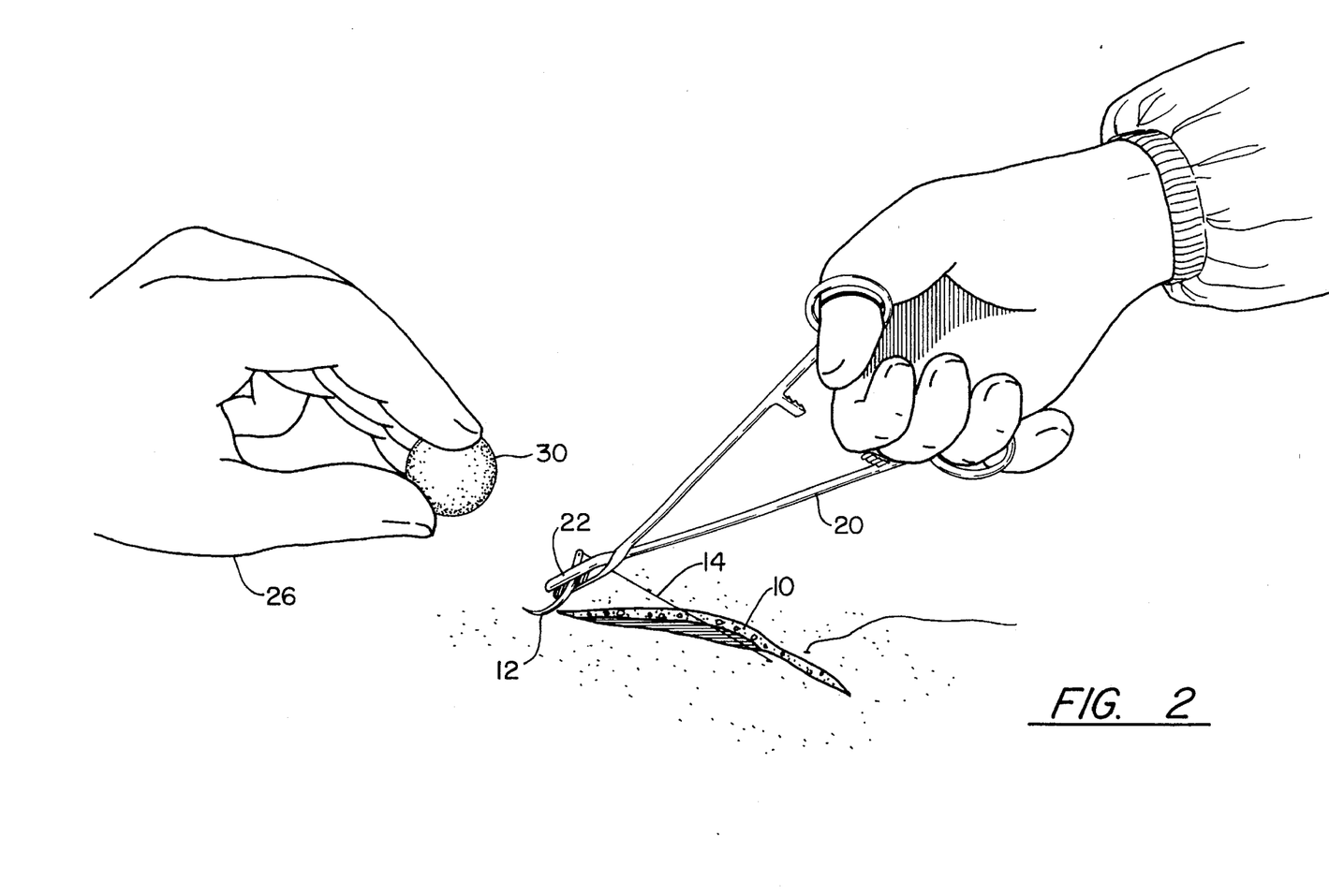
FIG. 2 is a perspective view illustrating the use of apparatus according to the invention.

There is shown in FIG. 1 the beginning of a suturing process. A wound 10 is to be closed with a suture needle 12 and suture 14. According to common surgical practice, a needle holder 20 can be utilized to grip the needle 12 for placement of the sutures. As shown in FIG. 2, the suture needle 12 is passed through the wound so as to draw the suture 14 through the wound, whereupon a suture knot must be tied to retain the suture in place.

Figure 3:
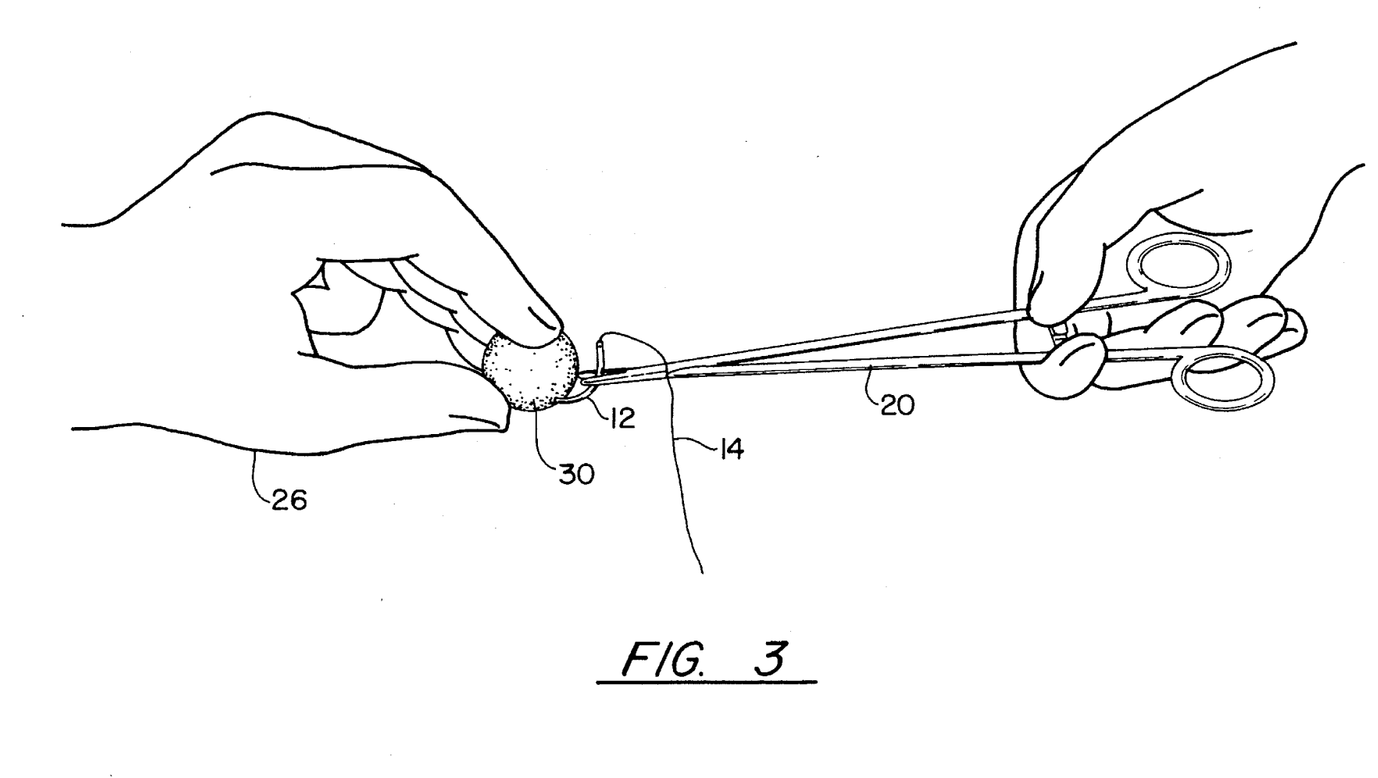
FIG. 3 is a side elevation illustrating placement of a suture needle into apparatus according to the invention.
Figure 4:
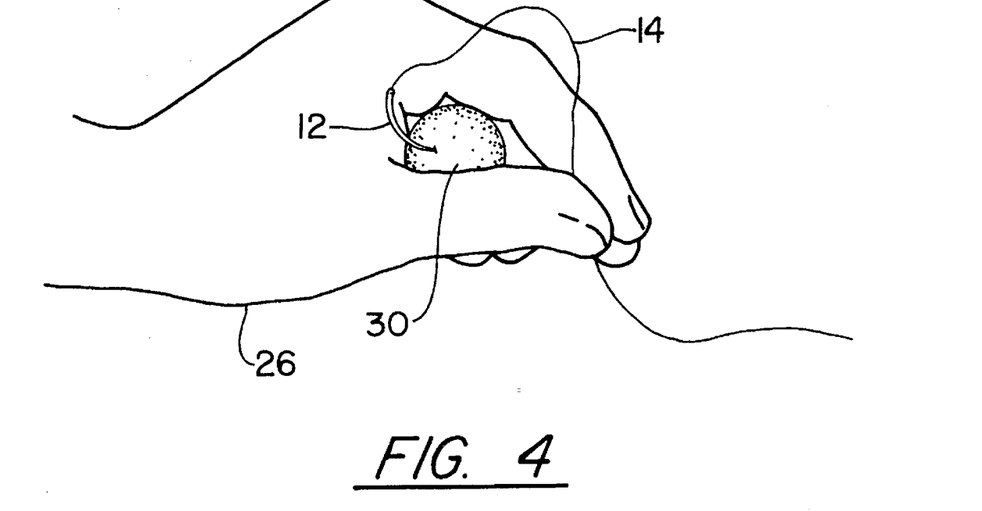
FIG. 4 is a side elevation illustrating the holding of a suture needle according to the invention.

The needle 12 is secured in jaws 22 of the needle holder 20. According to the invention, the needle holder 20 is then utilized to thrust the tip of the needle 12 into the retaining material of a retainer 30 (FIG. 3). The suture 14 can then be looped about the hand 26 of the physician, and the needle 12 and retainer 30 can be held in the hand or allowed to dangle freely without fear that the needle 12 will inadvertently puncture the hand and contaminate the physician with biological material from the patient (FIG. 4). The suture knot can then be tied according to customary practice.

Figure 5:
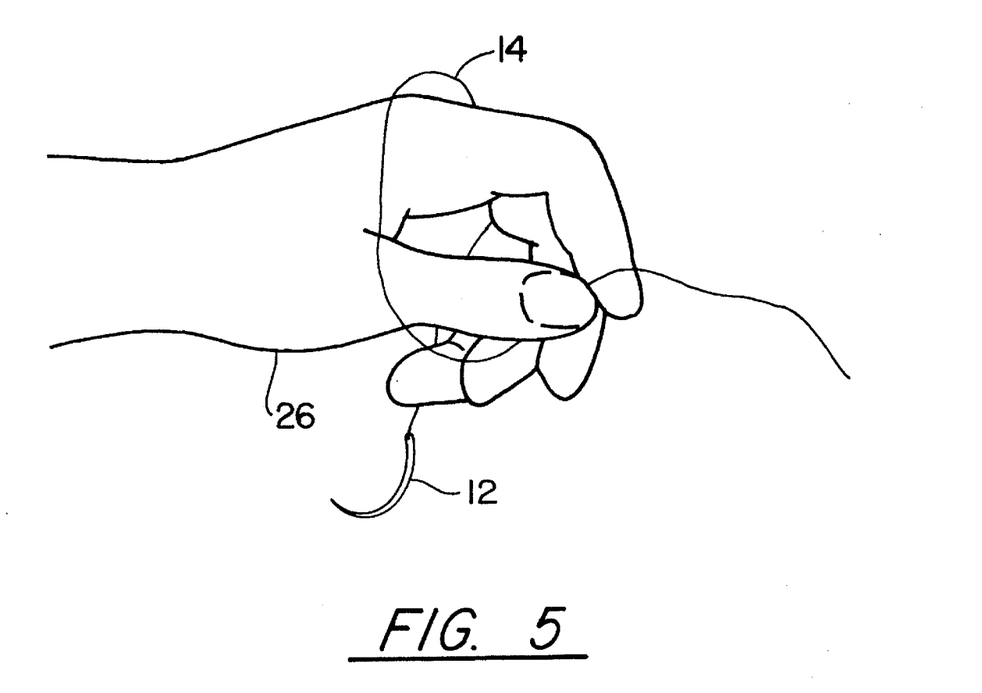
FIG. 5 is a side elevation illustrating the holding of a suture needle according to prior methods.

The invention provides a significant increase in safety over prior methods as illustrated in FIG. 5. Customary practice has the suture 14 draped about the needle holding hand, with the needle 12 dangling freely as illustrated. Alternatively, the needle is sometimes held between the fingers during the tying process. The needle 12 is free to puncture the hand of the physician both during the knot-tying process and also during manipulation into and out of the needle holder 20.

The needle 12 is then repositioned into the holder 20. The jaws 22 of the holder 20 are secured to the needle 12 in known fashion while the needle 12 is securely within the retainer 30. Needle sticks are thereby avoided. The holder 20 is again manipulated to place another suture, and the process is repeated as many times as are necessary to properly close the wound or tissue 10.

Figure 6:
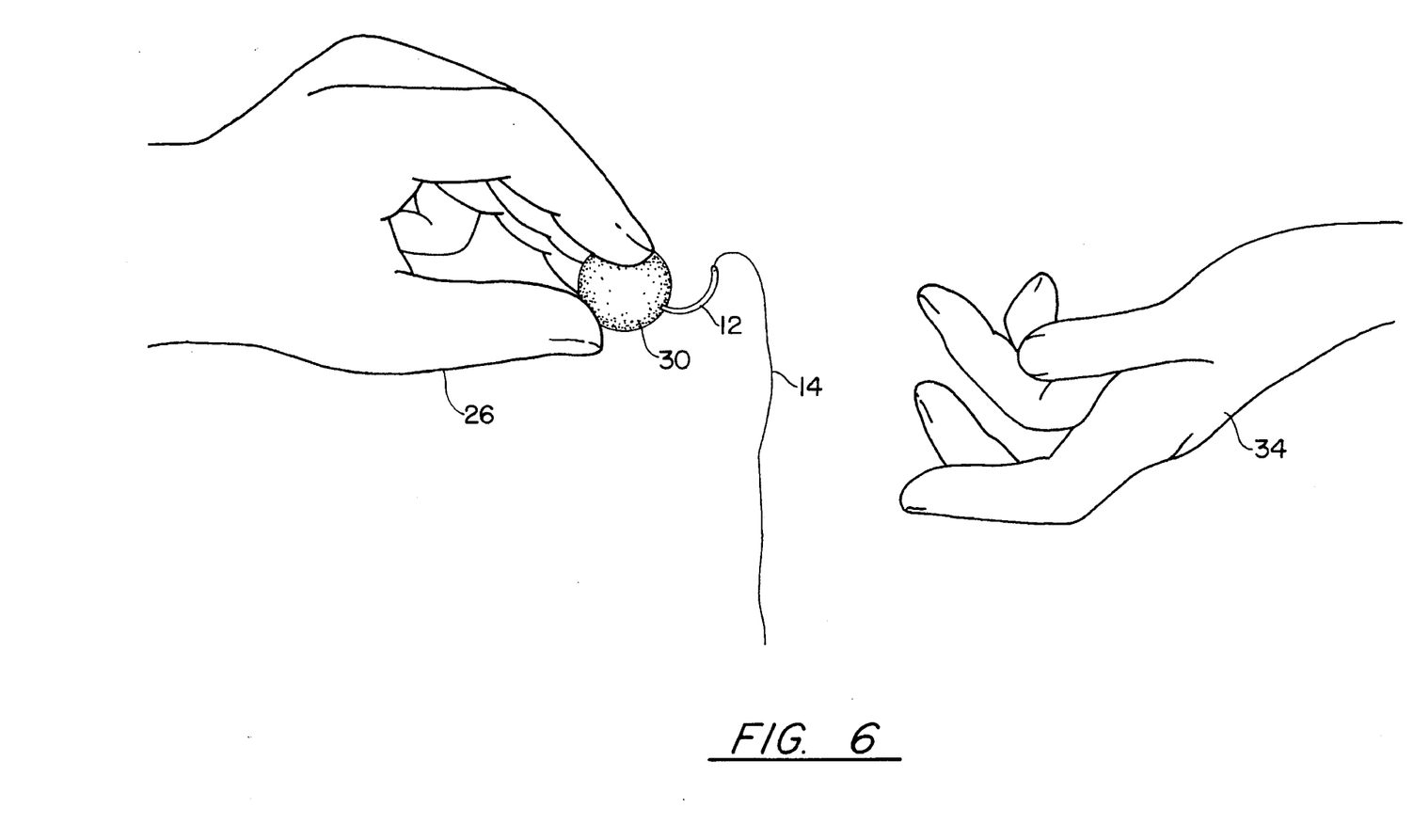
FIG. 6 is a side elevation illustrating the handling of a suture needle using the method and apparatus of the invention.

Completion of the suturing process requires that the needle 12 be handed to an assistant, who may then hand the needle to another person, the end result being that the needle is discarded as waste. The handling process is illustrated in FIG. 6. The needle 12 is secured again to the retainer 30, with whatever remains of the suture 14. The retainer 30 is then passed from the hand 26 of the physician to the hand 34 of an assistant. The point of the needle 12 is securely embedded within the retaining material of the retainer 30 such that the needle 12 can be passed safely and efficiently to the assistant for subsequent removal.

The retaining material is pervious to the tip of a suture needle, but must be rigid or semi-rigid so as to retain shape. The material should also not be brittle or frangible, so as to fragment and cause particles to potentially reach the wound or incision. Semi-rigid and elastic materials, such as silicone and natural and synthetic rubbers, are currently preferred. This list is not meant to be exhaustive, however, and other materials having the aforementioned properties, including rigid or semi-rigid styrofoams or other foam materials, could alternatively be utilized. The surface of the retaining material may be textured or roughened to resist slippage of the needle 12 over the surface of the retaining material.

The retainer must be sterile to avoid the possibility of infection to the patient. The retainer must either be made of a material which can be autoclaved or chemically treated for sterility, or must be wrapped in individual packaging which ensures sterility until immediately prior to use. The packaging should be hermetically sealed, but can be selected from a variety of packaging currently available including rigid containers or flexible packaging such as a foils or plastics.

Figures 7, 8, 9, 9A, 9B, 10, 10A:
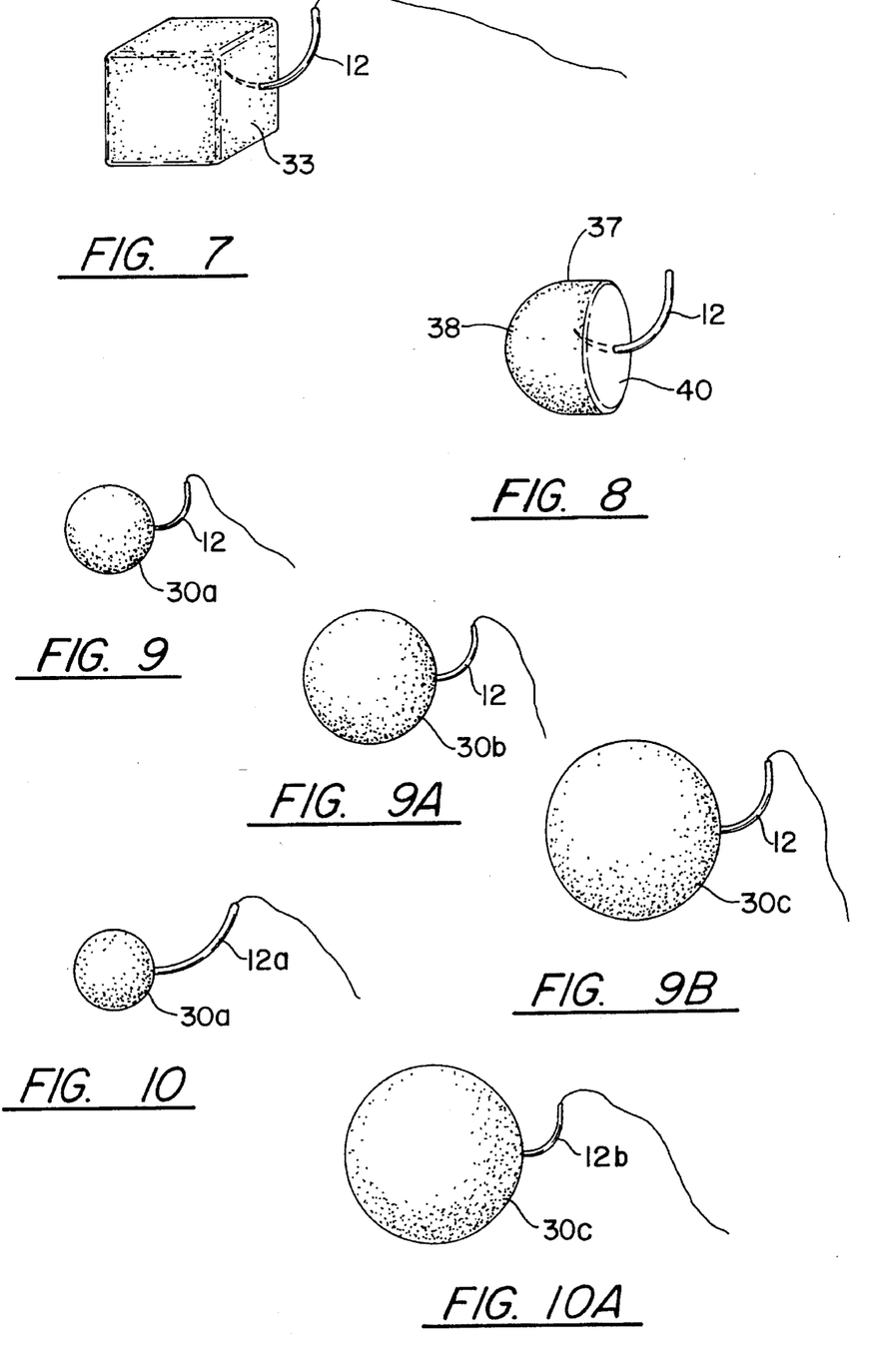
FIG. 7 is a perspective view, partially in phantom, of alternative apparatus according to the invention.
FIG. 8 is a perspective view, partially in phantom, of an alternative embodiment.
FIGS. 9, 9A, and 9B are side elevations illustrating alternative sizes of the invention.
FIGS. 10 and 10A are side elevations illustrating the use of alternative sizes with alternative suture needles.

The retainer can take a number of different shapes. A spherical shape, as shown in FIGS. 2–4, is currently preferred because this shape is comfortable and convenient in use. The particular usage and preferences of physicians may require alternative shapes. A rectangular shape is depicted for the retainer 33 in FIG. 7. This shape has the advantage that the flat faces of the retainer provide an even surface for thrusting the tip of the needle 12 into the retainer 33. This can help to prevent slippage of the needle past the retainer 33 during the insertion process. A semi-spherical retainer 37 is shown in FIG. 8. A substantially semi-spherical portion 38 is provided with which to hold and manipulate the retainer 37, and a flat surface 40 is provided through which to insert and embed the needle 12 into the retainer 37. This design combines the comfort and convenience of a spherical shape, with the benefits of a flat surface for insertion of the needle 12.

The retainer is dimensioned according to the preferences of the user and the size of the suture needle 12. Generally, however, sizes smaller than about ¼" in diameter or larger than about 3" in diameter are uncomfortable and unwieldy to work with. The retainer should be readily manipulated by one hand of the user. FIGS. 9, 9A, and 9B illustrate the use of spherical retainers 30a, b, and c having respectively increasing dimensions, with respectively increasing needle sizes. FIGS. 10 and 10A illustrate, according to the preference of the user, that the smaller dimension 30a can be utilized with a larger needle 12a, or a larger dimension 30c can be used with a smaller needle 12b.

The retainer can be comprised entirely of the retaining material. Structure can also be provided with the retainer to assist the user in grasping and/or manipulating the retainer. A strap, bracelet, finger ring or thimble can be secured to the retaining material. Alternatively, the retainer can be attached to an instrument, gown, or glove by structure such as hook and loop fasteners or other known attachment structure. Magnetic material can be included with the retainer to secure the retainer to a magnetized holder, and to also attract and retain the needle against accidental drops.

Figure 11:
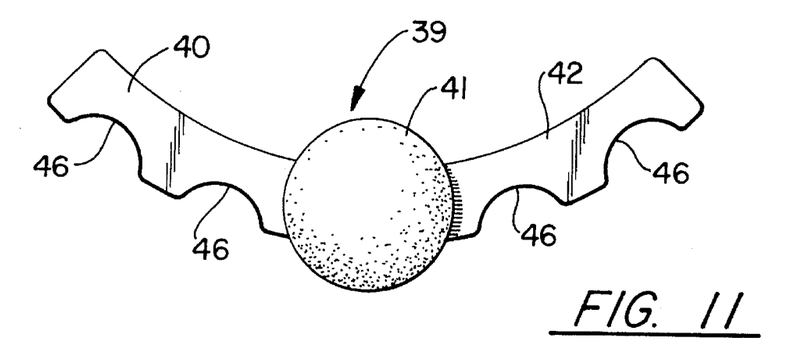
FIG. 11 is a top plan view of another alternative embodiment.
Figure 12:
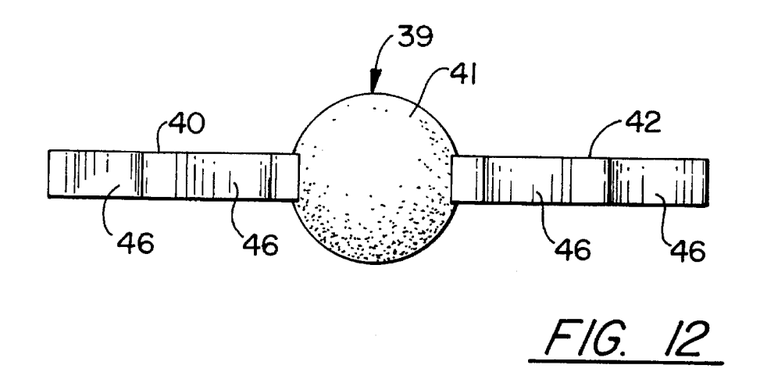
FIG. 12 is a front elevation of the embodiment of FIG. 11.
Figure 13:
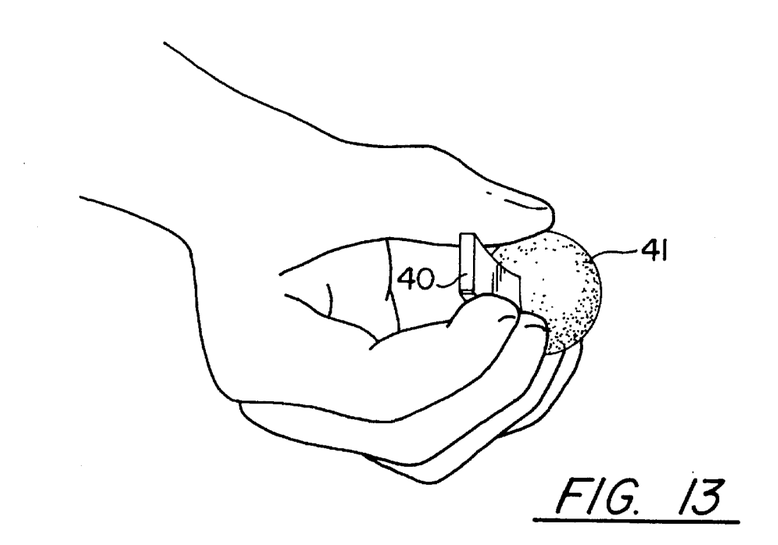
FIG. 13 is a perspective view illustrating the use of the embodiment of FIG. 11.

Another embodiment is disclosed in FIGS. 11–13. A retainer 39 has retaining material 41 and oppositely extending protrusions in the form of arms 40, 42. Grooves 46 are provided for the placement of the fingers. The thumb of the user steadies the device (FIG. 13) and the device can readily be manipulated as desired by the user. The arms 40, 42 provide a number of alternatives for holding and handling the retainer 39.

Figure 14:
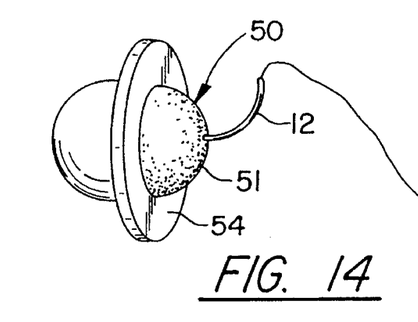
FIG. 14 is a perspective view of an alternative embodiment.
Figure 15:
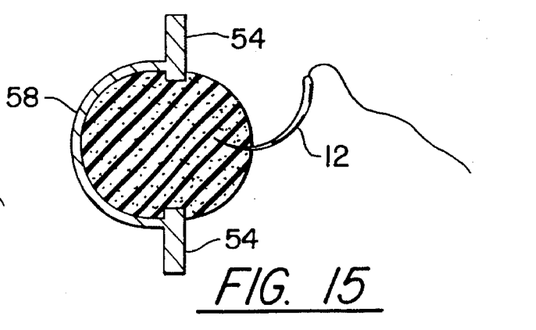
FIG. 15 is a cross section of the embodiment of FIG. 14.

An alternative retainer construction is shown in FIGS. 14–15. The retainer 50 has retaining material 51 and a substantially circumferential protrusion 54 which provides a surface for grasping and manipulating the retainer 50. The protrusion 54 is made of a substantially needle impervious material, which prevents or substantially retards penetration by the needle 12. Slippage of a needle 12 off of the retainer 50 during insertion will cause the needle 12 to strike the protrusion 54 and not the fingers or hands of the user. A needle impervious cap 58 can be provided over a portion of the retainer 50 to protect the hand of the user from penetration of the needle 12 completely through the retaining material 51, where the needle 12 could prick the user.

Figure 16:
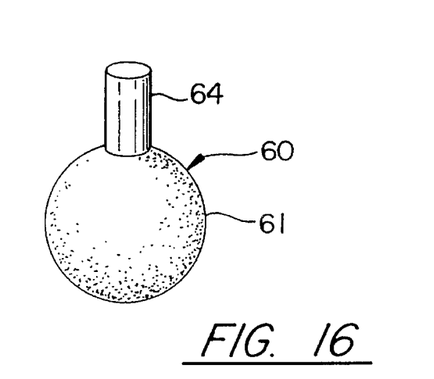
FIG. 16 is a perspective view of still another alternative embodiment.

Another embodiment is shown in FIG. 16 in which a retainer 60 includes retaining material 61 and a single protrusion in the form of cylinder 64 to assist the user in the manipulating the retainer 60.

Figure 17:
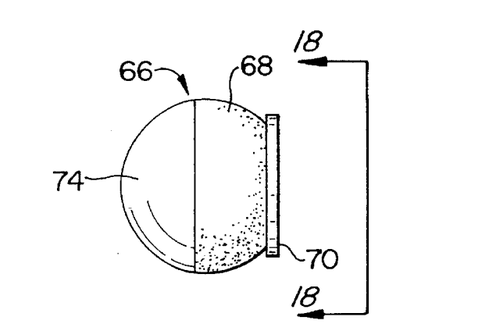
FIG. 17 is a side elevation of yet another alternative embodiment.
Figure 18:
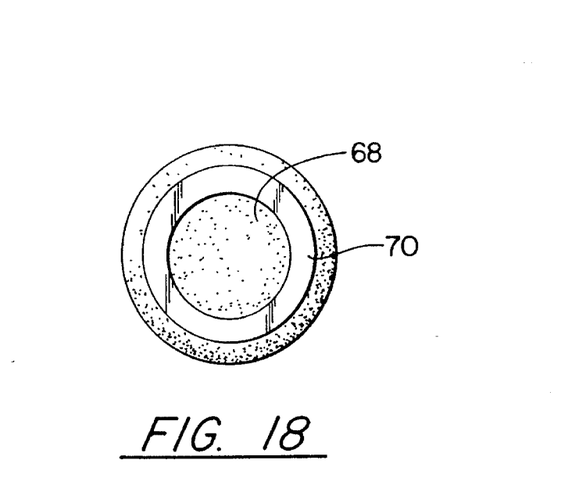
FIG. 18 is an elevation taken along line 18—18 in FIG. 17.

The retainer 66 FIGS. 17–18 includes retaining material 68 and a raised needle guard 70 of needle impervious material, in this embodiment in the shape of a ring. The guard 70 permits the insertion of a needle 12 within the center of the ring, but will block slippage of the needle over the surface of the retaining material 68 in a manner which could prick the user. A needle impervious cap 74 or other material is provided to prevent the unintentional passage of the needle through the retaining material 68, where it could prick the user or others who handle the retainer 66 during the disposal process. The needle impervious cap 74 is preferably made of a hard plastic or metal. It is alternatively possible that the cap 74 could be replaced by structure imbedded within the retaining material 68.

This invention can be embodied in other forms without departing from the spirit or essential attributes thereof. Features shown in the embodiment can be combined with features shown in other embodiments or with other known features to create new embodiments with the scope of the invention. Reference should be had to the following claims, rather than to the foregoing specification, as indicating the scope of the invention.

I claim:

1. A method for suturing the body with a suture needle, comprising the steps of:

grasping in one hand a device made entirely of a sterile, needle pervious material capable of retaining said needle when the point of the needle is thrust into the material and sized to completely fit within an enclosed hand;

placing a suture with the suture needle into the body;

thrusting the tip of the suture needle contaminated with biological material into the needle retaining material;

supporting the needle retaining material with the hand and substantially above the wound;

tying a suture knot; and removing the needle from the needle retaining material, and repeating the above until the suturing process is completed.

2. The method of claim 1, further comprising the step of handing said contaminated suture needle and said retaining material to an assistant while the needle is retained by said retaining material.

3. A method for tying suture knots in a body with a suture that is attached at one end to a wound and at the other end to a needle, comprising the steps of:

grasping in one hand a device made entirely of a sterile, needle pervious retaining material and sized to completely fit within an enclosed hand;

thrusting the tip of the suture needle into the needle retaining material;

supporting the needle and needle retaining material with the hand; and, tying a suture knot with the suture.

* * * * *